United States Patent [19]

Cerwin et al.

[11] 4,249,656
[45] Feb. 10, 1981

[54] SUTURE PACKAGE

[75] Inventors: Robert J. Cerwin, Pittstown; Robert H. Yolinsky, Bridgewater, both of N.J.

[73] Assignee: Ethicon, Inc., Somerville, N.J.

[21] Appl. No.: 84,921

[22] Filed: Oct. 15, 1979

[51] Int. Cl.³ .............................................. A61L 17/02
[52] U.S. Cl. .................................... 206/63.3; 206/380
[58] Field of Search .............. 206/63.3, 227, 380, 206/381, 382

[56] References Cited

U.S. PATENT DOCUMENTS

| 3,444,994 | 5/1969 | Kaepernik et al. | 206/63.3 |
|---|---|---|---|
| 3,939,969 | 2/1976 | Miller et al. | 206/63.3 |
| 4,063,638 | 12/1977 | Marwood | 206/63.3 |
| 4,069,912 | 1/1978 | Black et al. | 206/63.3 |
| 4,120,395 | 10/1978 | Mandel et al. | 206/63.3 |
| 4,135,623 | 1/1979 | Thyen | 206/63.3 |
| 4,142,628 | 3/1979 | Marocco et al. | 206/63.3 |

Primary Examiner—Joseph Man-Fu Moy
Attorney, Agent, or Firm—Wayne R. Eberhardt

[57] ABSTRACT

An improved package for needled sutures comprising a folded suture retainer wherein a coiled suture is contained between two folded panels while the needle is contained between two adjacent folded panels. A gusset along the foldline between the needle retention panels and the suture retention panels provides a channel for the length of suture traversing the foldline and facilitates the easy withdrawal of the suture from between the panels of the folded retainer.

13 Claims, 4 Drawing Figures

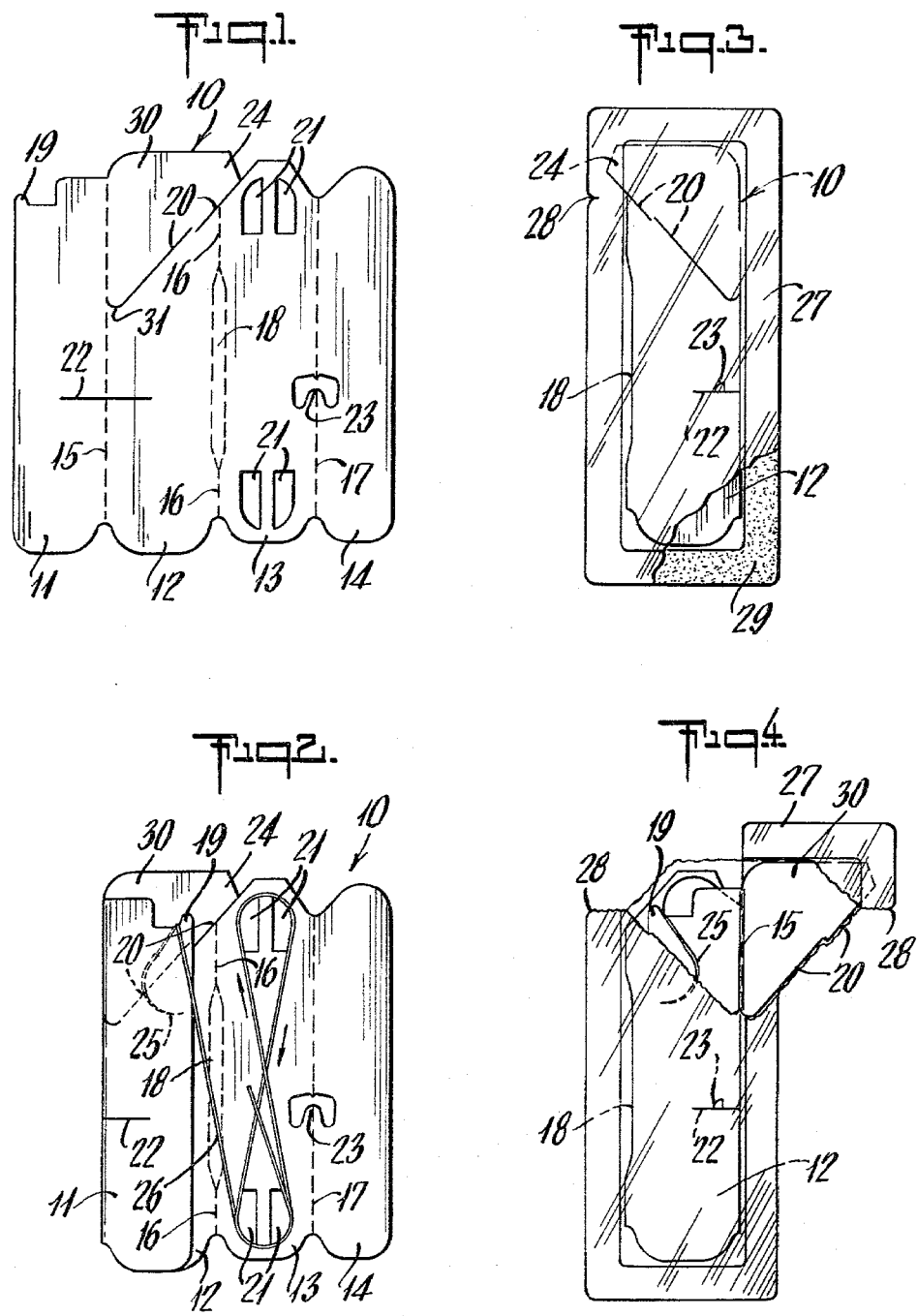

SUTURE PACKAGE

BACKGROUND OF THE INVENTION

This invention relates to packages for surgical sutures, and, more particularly, to a multipaneled, folded paper retainer for a coiled suture and a needle attached thereto.

Packages for surgical sutures are constructed according to the nature of the suture and its intended use. In general, the ideal package holds and protects the suture during handling and storage yet allows the suture to be readily removed with a minimum of handling and difficulty.

A popular suture package consists of a folded paper suture retainer contained in a sterile, hermetically sealed envelope. The sterility of the suture and envelope are maintained by a second sealed outerwrap. When the suture is to be used, the outerwrap is opened in the operating room and the sealed envelope deposited in a sterile area. Sterile personnel thereupon tear open the sterile envelope to gain access to the suture.

Suture packages have recently been designed to simplify opening of he sterile envelope and improve accessibility of the suture in order to avoid unnecessary delays during surgical procedures. A major improvement in this regard is described in U.S. Pat. No. 3,939,696 where a portion of the inner suture retainer is secured to the sealed envelope so that the envelope and inner retainer may be opened simultaneously, and the end of the suture exposed for immediate pickup.

The present invention represents a further improvement in packages of this type where the end of the suture is automatically presented when the sterile envelope is opened. Packages of the present invention have advantages in both manufacture and use, particularly, in regard to needle placement and the use of automatic winding to coil the suture within the retainer.

It is accordingly an object of the present invention to provide an improved package for needled sutures. It is a further object of the present invention to provide an improved folded paper retainer for single strand surgical sutures having a needle preattached thereto. It is an additional object of this invention to provide a suture package which allows simultaneous opening of the inner suture retainer and outer sealed envelope to provide instant access to the suture. These and other objects of the invention will be apparent from the ensuing description and claims.

SUMMARY

The present invention provides an elongated, four-panel, folded suture retainer for a needled suture. The armed end of the suture is retained between first and second panels while the bulk of the suture length is coiled between third and fourth panels. The foldline between the second and third panels which is traversed by the suture strand is provided with a gusset over a substantial portion of the length thereof. When the retainer is fully folded, the gusset creates a channel in the interior of the package through which the initial portion of the suture is drawn when the suture is removed from the retainer.

When the retainer is in its fully folded position, the first and fourth panels are enclosed between the second and third panels which then form the outside front and back panels of the folded retainer. The second panel is provided with a die cut diagonal tearline extending from one corner across the width of the panel which allows a portion of this panel to be removed in order to gain access to the needle retained between the first and second panels. Upon removal of this portion of the second panel, the needle is readily grasped with a needle holder, and the suture withdrawn from between the folds of the retainer. The initial length of suture which traverses the foldline between the second and third panels is readily withdrawn with minimum resistance through the channel formed by the gusset in that foldline.

The suture retainer is sterilized and sealed within a conventional sterile envelope which preferably comprises aluminum foil coated with a thermoplastic polymer and heat sealed around the periphery thereof. In a preferred embodiment of the present invention, the portion of the second panel intended to be removed to gain access to the suture needle is provided with a tab extending beyond the width of the folded retainer. This tab is sealed in the border of the outer envelope so that when the envelope is opened by tearing one end, the portion of the second panel is simultaneously opened to expose the needled end of the suture. Thus, the present invention provides one step access to the suture contained within the package.

DESCRIPTION OF DRAWINGS

FIG. 1 is a plan view of an unfolded suture retainer of the present invention.

FIG. 2 is a plan view of the retainer of FIG. 1 illustrating the position of the needle and suture strand in a partially folded retainer.

FIG. 3 is a plan view of the fully folded suture retainer of FIG. 2 contained within a sealed outer envelope.

FIG. 4 is a plan view of the suture package and envelope of FIG. 3 opened to provide access to the suture needle.

DETAILED DESCRIPTION OF PREFERRED EMBODIMENT

FIGS. 1 through 4 illustrate the various stages in preparing and using an exemplary suture package of the present invention. In FIG. 1 there is illustrated an open suture retainer 10 comprising needle cover panel 11, needle retaining panel 12, suture retaining panel 13, and suture cover panel 14. Foldlines 15, 16, and 17 are provided between the respective panels to facilitate rapid folding and assembly of the retainer. Additionally, foldline 16 is provided with a central gusset section 18 over a substantial portion of the length thereof, the purpose of which will be apparent from the description below.

Panel 12 is divided into two sections by interrupted die cut 20 extending diagonally across the width thereof to form needle access panel 30 over the upper portion of panel 12 as illustrated. The free edge of needle access panel 30 extends beyond foldline 16 forming tab 24 which extends beyond the width of the folded retainer as hereinafter described. Die cut 20 terminates in upturn 31 at foldline 15, the purpose of which is explained below.

Other features of the retainer illustrated in FIG. 1 include tip 19 extending beyond the end of panel 11 and winding pin openings 21 in panel 13. Die cut 22 extending across foldline 15 and tab 23 formed by a cutout in foldline 17 provide a cooperating slot and tab lock for the fully folded retainer.

Referring now to FIG. 2, there is illustrated a partially folded retainer with a surgical suture positioned thereon. In placing the suture in the retainer, needle 25 with suture 26 attached thereto is placed on panel 12, preferably over die cut 20 as illustrated. Panel 11 is folded over needle 25 and a short length of suture immediately adjacent thereto, and the remainder of the suture is passed over the top of panel 11 and wound around winding pins (not shown) projecting through openings 21 in panel 13. Tab 19 extending from the upper end of panel 11 prevents suture 26 from slipping off the edge of panel 11 during winding and folding of the suture in the retainer. The suture is preferably wound in a figure-8 coil configuration and in the directions indicated by the arrows shown on FIG. 2. The suture in FIG. 2 is shown as only a single figure-8 coil for clarity of illustration, it being understood that in practice, the bulk of the suture would be wound in a plurality of sequential, superimposed coils in the illustrated manner.

After the full length of suture has been wound on panel 13, the winding pins are withdrawn and panel 14 is folded over panel 13 to enclose the coiled suture. The retainer is then folded along line 16 to fully enclose the needle and suture and the retainer is locked in its folded position by means of slot 22 and tab 23. This final fold forms gusset 18 which creates a space between panels 12 and 13 where suture 26 traverses foldline 16.

The fully folded suture retainer is subsequently sterilized and sealed within sterile outer envelope 27 as illustrated in FIG. 3. Tab 24 projecting beyond the width of the folded retainer is secured in the seal area of envelope 27 as illustrated. Tear notch 28 is provided in the outer edge of enveloped 27 and located approximately opposite lower edge of tab 24 to facilitate opening of the suture package by tearing the outer envelope.

Envelope 27 is a conventional suture package envelope formed by heat sealing two panels of aluminum foil coated on the interior surfaces thereof with a heat sealable polymeric composition 29. The envelope is bonded around the periphery of the inner suture retainer as illustrated in FIG. 3. Other means for sealing the envelope may be employed at the discretion of the practitioner.

Sutures packaged as illustrated in FIG. 3 are sterile and hermetically sealed and may be stored for extended periods of time. When the suture is to be removed from the package, the outer envelope is opened by tearing from notch 28 as illustrated in FIG. 4. In the illustrated embodiment where tab 24 is secured in the seal line of envelope 27, needle access panel 30 of panel 12 is simultaneously removed as the envelope is opened. As access panel 30 opens, envelope 27 is made to tear diagonally across the width of the suture package guided by the edge of die cut 20. Needle 25 is thereby exposed and can be readily grasped with a needle holder in order to withdraw the suture from between the folds of the inner suture retainer without removing the paper retainer from the foil envelope.

An additional feature of the illustrated package which is a preferred but not essential feature is upturn 31 of die cut 20 at foldline 15. This feature allows needle access panel 30 and the portion of envelope 27 secured thereto to be readily removed from the opened package by tearing along foldline 15. Removal of this portion of the opened package allows the inner suture retainer to be withdrawn from the foil envelope in its folded condition and with the needle and suture contained therein.

Tab 24 is an optional feature of the suture retainer of the present invention and may be omitted if desired to provide a suture package wherein the suture retainer is intended to be removed from the outer envelope before removing the suture from the retainer.

The suture retainer of the present invention is preferably constructed of a heavy weight, relatively stiff paper or paperboard such as 5 point to 12 point solid, bleached sulfate board. This paperboard is readily foldable and yet sufficiently strong and stiff to support the suture and provide a relatively rigid package. Similar materials including plastics, foils and laminates of these with each other or with paper can also be readily cut from such materials by a single die which also forms the desired foldlines including the necessary gusset in accordance with the present invention.

The preceding description has been directed primarily to a preferred embodiment of the present invention and many variations in which nevertheless employ the essential features thereof will be apparent to those skilled in the art. Such variations are accordingly included within the scope of the present invention.

What is claimed is:

1. An elongated, folded retainer for needled surgical sutures comprising
   (a) first needle cover panel;
   (b) a second needle retaining panel foldably connected to said needle cover panel along one major edge thereof;
   (c) a third suture retaining panel foldably connected to said needle retaining panel along the other major edge thereof;
   (d) a fourth suture cover panel foldably connected to said suture winding panel along the other major edge thereof;
   said needle retaining panel having a die cut extending diagonally across the width thereof to define a separate needle access panel;
   said foldline between said needle retainng panel and said suture retaining panel including a gusset over a substantial portion thereof;
   whereby when said retainer is in its folded configuration with a needled suture contained therein, said surgical suture extends from said needle retaining panel across said gusset to said suture retaining panel, and said gusset in combination with said panels forms a channel through which the suture traversing said panels may be drawn when removing said suture from said retainer.

2. A retainer of claim 1 wherein said die cut across said needle retaining panel extends from the outside edge adjacent said suture retaining panel to the foldline adjacent said needle cover panel.

3. A retainer of claim 1 wherein a portion of said needle access panel extends beyond the foldline between said second and third panels.

4. A retainer of claim 1 having integral locking means to secure said retainer in its folded configuration.

5. A retainer of claim 4 wherein said locking means comprises a tab bridging the foldline between said third and fourth panels and a corresponding cooperating slat bridging the foldline between said first and second panels, whereby when said retainer is in its folded configuration, said tab engages said slot in a locking relationship.

6. A suture package comprising in combination a folded retainer of claim 1 and a needled suture, the needle of said suture being positioned between said first and second panels with the suture extending from between said panels, said suture traversing the near end of said first panel and extending across the foldline and gusset between said second and third panels with the bulk of said suture being coiled between said third and fourth panels.

7. A suture package of claim 6 wherein said needle traverses the die cut in said second panel.

8. A suture package of claim 6 wherein said suture is coiled between said third and fourth panels in a figure-8 configuration.

9. A suture package of claim 6 enclosed in an outer envelope sealed around the periphery thereof.

10. A suture package of claim 9 wherein a portion of said needle access panel extends beyond the foldline between said second and third panels and is secured in the seal around the periphery of said outer envelope.

11. A suture package of claim 6 wherein said retainer is secured in its folded configuration by integral locking means.

12. A suture package of claim 6 wherein said needle is curved, and is positioned with the outside of the curve oriented toward the foldline between said first and second panels.

13. A suture package of claim 6 wherein the edge of said first panel traversed by said suture includes a suture retaining tab extending from said edge of said panel.

* * * * *